United States Patent
He et al.

(12) 
(10) Patent No.: US 6,509,371 B1
(45) Date of Patent: Jan. 21, 2003

(54) COMPOSITIONS CONTAINING BERGAMOTTIN FOR INCREASING THE ORAL BIOAVAILABILITY OF PHARMACEUTICAL AGENTS

(75) Inventors: Kan He, Ann Arbor, MI (US); Paul F. Hollenberg, Ann Arbor, MI (US); Thomas F. Woolf, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/486,117

(22) PCT Filed: Aug. 11, 1998

(86) PCT No.: PCT/US98/16579
§ 371 (c)(1),
(2), (4) Date: Apr. 21, 2000

(87) PCT Pub. No.: WO99/08676
PCT Pub. Date: Feb. 25, 1999

Related U.S. Application Data

(60) Provisional application No. 60/056,129, filed on Aug. 19, 1997.

(51) Int. Cl.$^7$ .............................................. A61K 31/35
(52) U.S. Cl. ..................................................... 514/455
(58) Field of Search ........................................ 514/455

(56) References Cited

U.S. PATENT DOCUMENTS

| | | |
|---|---|---|
| 5,665,386 A | 9/1997 | Benet et al. |
| 5,716,928 A | 2/1998 | Benet et al. |
| 6,004,927 A | 12/1999 | Benet et al. |
| 6,160,006 A * | 12/2000 | Edwards et al. ............ 514/455 |

FOREIGN PATENT DOCUMENTS

| | | |
|---|---|---|
| JP | 07025764 A * | 1/1995 |
| WO | 9640192 | 12/1996 |

OTHER PUBLICATIONS

"Identification of nonvolatile components in lemon peel by high-performance liquid chromatography with confirmation by mass spectormetry and diode–array detection", Baldi et al, 1995, Journal of Chromatography A, 718, 89–97.*
"Synthesis of bergamottin", Chatterjee et al., J. Chem. Soc., 1961, 2246–7, abstract.*
"Fluorescent substances in the essence of lemon, bergamot, tangerine, bitter orange, and sweet orange", D'Amore et al., 1965, Rass. Chim, 17(6), 264–9, abstract.*
"Chemical Compositions of lemon oil. Isolation of a series of substituted coumarins", Stanley et al, J. Am. Chem. Soc., 1957, 79, 3488–91, abstract.*
Bailey, D. et al., "Interaction of Citrus Juices With Felodipine And Nifedipine", *The Lancet*, vol. 337, pp. 268–269 (Feb. 2, 1991).
Ducharme, M. et al., "Disposition Of Intravenous And Oral Cyclosporine After Administration With Grapefruit Juice", *Clinical Pharmacology & Therapeutics*, vol. 57, No. 5, pp. 485–491 (May 1995).
Edwards, D. et al., "Accelerated Communication Identification Of 6',7'–Dihydroxybergamottin, A Cytochrome P450 Inhibitor, In Grapefruit Juice", *Drug Metabolism And Disposition*, vol. 24, No. 12, pp. 1287–1290 (Dec. 1996).
Kupferschmidt, H. et al., "Interaction Between Grapefruit Juice And Midazolam In Humans",*Clinical Pharmacology & Therapeutics*, vol. 58, No. 1, pp. 20–28 (Jul. 1995).
Soons, P. et al., "Grapefruit Juice And Cimetidine Inhibit Stereoselective Metabolism Of Nitrendipine In Humans", *Clinical Pharmacology & Therapeutics*, vol. 50, No. 4, pp. 394–403 (Oct. 1991).
Cai Yingna Mike J: "Inhibition And Inactivation Of Murine Hepatic Ethoxy–And Pentoxyresorufin O–Dealkylase By Naturally Occurring Coumarins." Chemical Research in Toxicology, 1993, XP002089060.
Ducharme M P Et Al: "Trough Concentrations Of Cyclosporine In Blood Following Administration With Grapefruit Juice" British Journal of Clinical Pharmacology, vol. 36, No. 5, 1993, pp. 457–459, XP000612518.
Bailey D G Et Al: "Grapefruit Juice And Drugs. How Significant Is The Interaction?" Clinical Pharmacokinetics, vol. 26, No. 2, 1994, pp. 91–98, XP000612514.

* cited by examiner

*Primary Examiner*—Zohreh Fay
*Assistant Examiner*—Brian-Yong S. Kwon
(74) *Attorney, Agent, or Firm*—Merchant & Gould P.C.

(57) ABSTRACT

Bergamottin, principle compound in grapefruit juice responsible for inhibition of p450 3a4, the predominant p450 enzyme in the intestine, is coadministered with a compound having low bioavailability to a patient to increase oral bioavailability of the compound and pharmaceutical compositions of the same, as well as a method of isolating bg from grapefruit juice.

6 Claims, 17 Drawing Sheets

COMPOSITIONS CONTAINING BERGAMOTTIN FOR INCREASING THE ORAL BIOAVAILABILITY OF PHARMACEUTICAL AGENTS

This application claims the benefit of Provisional Application No. 60/056,129, filed Aug. 19, 1997.

This application is a 371 of PCT/US98/16579 Aug. 11, 1998.

BACKGROUND OF THE INVENTION

The present invention relates to a method of increasing the oral bioavailability of compounds by coadministration of the compound with Bergamottin (BG) to a patient. More particularly, the present invention concerns the use of BG to inhibit the intestinal enzymatic metabolism of compounds having low bioavailability. Specifically, inhibition of intestinal cytochrome P450 3A4 by BG decreases the intestinal metabolism of the compounds and increases their oral bioavailability. Additionally, the present invention relates to pharmaceutical compositions which include BG in combination with a compound having low bioavailability and a pharmaceutically acceptable carrier. Finally, the present invention relates to a method of isolating BG from grapefruit juice.

Oral bioavailability is defined as the fraction of unchanged drug reaching the systemic circulation following administration by the oral route. Bioavailability generally can be defined as the fraction of unchanged drug reaching the systemic circulation following administration to a patient through any treatment route. Enhancing bioavailability of pharmaceutical agents has drawn a lot of attention for drug development and clinical pharmacology. Since P450 1A4 is the major P450 enzyme expressed in the intestines and is involved in the metabolism of a broad spectrum of clinically used drugs, it is considered to be one of the major determinant for oral bioavailability of these drugs. Some costly drugs, such as cyclosporine, FK506, taxol, indinavir, saquinavir and etc., are found to be metabolized extensively by P450 3A4. Coadministration of some of these drugs with P450 3A4 inhibitors have been found to increase their bioavailability.

Oral coadministration of grapefruit juice has been demonstrated to significantly increase the oral bioavailability of several clinically used drugs including dihydropyridines (Bailey D. G., Spence J. D., Munoz C., and Arnold J. M. O. Interaction of citrus juices with felodipine and nifedipine. *Lancett*, 1991;337:268–269 and Bailey D. G., Arnold J. M. O., Bend J. R., Tran L. T., and Spence J. D. Grapefruit juice—felodipine interaction: reproducibility and characterization with the extended release drug formulation. *Br. J. Clin. Pharmacol*, 1995;40:135–140), cyclosporine A (Ducharme M. P., Warbasse L. H., characterization with the extended release drug formulation *Br. J. Clin. Pharmacol,* 1995;40:135–140), cyclosporine A (Ducharme M. P., Warbasse L. H., and Edwards D. J. Disposition of intravenous and oral cyclosporine after administration with grapefruit juice. *Clin. Pharmacol. Ther.,* 1995;57:485–491), midazolam (Kuferschmidt H. H., Ha H. R., Ziegler W. H., Meier P. J., and Krahenbuhl S. Interaction between grapefruit juice and midazolam in humans, *Clin. Pharmacol. Ther.,* 1995;58:20–28), triazolam (Hukkinen S. K., Varhe A., Olkkola K. T., and Neuvonen P. J. Plasma concentrations of triazolam are increased by concomitant ingestion of grapefruit juice. *Clin. Pharmacol. Ther.,* 1995;58:127–131), terfenadine (Benton R. E., Hoig P. K., Zamaani K., Cantilena L. R., and Woosley R. L. Grapeffuit juice alters terfenadine pharmacokinetics, resulting in prolongation of repolarization on the electrocardiogram. *Clin. Pharmacol. Ther.,* 1996;59:383–388), and ethinyl estradiol (Weber A., Jager R., Borner A., Klinger G., Vollanth R., Mathey K., and Balogh A. Can grapefruit juice influence ethinylestradiol bioavailability? *Contraception,* 1996;53:41–47). Since all of these drugs are metabolized primarily by cytochrome P450 3A4, the predominant intestinal and hepatic P450 enzyme (Shimada T., Yamazaki H., Mimura M., Inui Y., and Guengerich F. P. Interindividual variation in human liver cytochrome P-450 enzymes involved in the oxidation of drugs, carcinogens and chemicals: studies with liver microsomes of 30 Japanese and 30 Caucasians. *J. Pharmacol. Exp. Ther.,* 1994;270:414–422 and Watkins P. B., Wrighton S. A., Schuetz E. G., Molowa D. T., and Guzelian P. S. Identification of glucocorticoid—inducible cytochrome P-450 in the intestinal mucosa of rats and man. *J. Clin. Invest.,* 1987;80:1029–1036), suggested that the grapefruit juice effect may be due to the inhibition of P450 3A4 activity. More recently, grapefruit juice has been shown to dramatically decrease the immunoreactive P450 3A4 content in enterocytes of human intestines with no change in the content of P450 3A4 mRNA (Lown K. S., Bailey D. G., Fontana R. J., Janardan S. K., Adair C. H., Fortlage L. A., Brown M. B., Guo W., and Watkins P. B. Grapefruit juice increases felodipine oral bioavailability in humans by decreasing intestinal CYP 3A protein expression. *J. Clin. Invest.,* 1997;99:1–9). These results suggest that the degradation of P450 3A4 protein may be accelerated by ingestion of grapefruit juice (Lown, Supra, 1997). Because suicide inactivation of rat P450 3A could accelerate degradation of the apoP450 (Correia M. A., Davoll S. H., Wrighton S. A., and Thomas P. E. Degradation of rat liver cytochrome P450 3A after their inactivation by 3,5-dicarbethoxy-2,6-dimethyl-4-ethyl-1,4-dihydropyridine: characterization of the proteolytic system. *Arch. Biochem. Biophys.,* 1992;297:228–238), mechanism based-inactivation of P450 3A4 has been suggested to be involved in grapefruit juice effects.

In order to identify the principle components in grapefruit juice responsible for increasing the bioavailability of some drugs, flavonoids, such as naringenin, naringin, quercetin, and kaemferol, have been chosen as possible candidates because they have been shown to competitively inhibit P450 3A4 activity in vitro (Miniscalco A., Lundahl J., Regardh C. G., Edgar B., and Eriksson U. G. Inhibition of dihydropyridine metabolism in rat and human liver microsomes by flavonoids found in grapefruit juice. *J. Pharmacol. Exp. Ther.,* 1992;261;1195–1199 and Ghosal A., Satoh H., Thomas P. E., Bush E., and Moore D. Inhibition and kinetics of cytochrome P450 3A4 activity in microsomes from rat, human and cDNA-expressed human cytochrome P450. *Drug Metab. Dispos.,* 1996;24:940–947). However, oral administration of these flavonoids did not produce the grapefruit juice effects (Bailey D. G., Arnold J. M. O., Munoz C., and Spence J. Grapefruit juice—felodipine interaction: mechanism, predictability, and effect of naringin. *Clin. Pharmacol. Ther.,* 1993;53;637–642 and Rashid J., McKinstry C., Renwick A. G., Dirnhuber M., Waller D. G., and George C. F. Quercetin, an in vitro inhibitor of CYP3A, does not contribute to the interaction between nifedipine and grapefruit juice. *Br. J. Clin. Pharmac.,* 1993;36:460–463). Recently, HPLC purification of methylene chloride extract of grapefruit juice led to the identification of 6',7'-dihydroxybergamottin as a component of grapefruit juice which caused inhibition of testosterone 6β-hydroxylase in liver microsomes from dexamethasone-induced rats (Edwards D. J., Bellevue F. H., III, and Woster P. M. Identification of 6',7'-dihydroxybergamottin, a cytochrome P450 inhibitor, in grapefruit juice. *Drug Metab. Dispos.,* 1996;24:1287–1290).

We have surprisingly and unexpectedly found that BG is the primary compound in grapefruit juice responsible for the mechanism-based inhibition of human cytochrome P450 3A4. Thus, coadministration of a compound having low oral bioavailability in combination with BG can be used to increase the oral bioavailability of the compound.

SUMMARY OF THE INVENTION

Accordingly, a first embodiment of the present invention provides a method of inhibiting enzymatic intestinal metabolism of a compound having low bioavailability comprising administering the compound in combination with BG to a patient.

A still further embodiment of the present invention is a pharmaceutical composition for administering an effective amount of a compound having low bioavailability in combination with BG in unit dosage form.

Finally, the present invention is directed to a method of isolating BG from grapefruit juice.

BRIEF DESCRIPTION OF THE DRAWINGS

The invention is further described by the following non-limiting examples which refer to the accompanying FIGS. 1 to 8, short particulars of which are given below.

DETAILED DESCRIPTION OF THE INVENTION

Figure 1A:
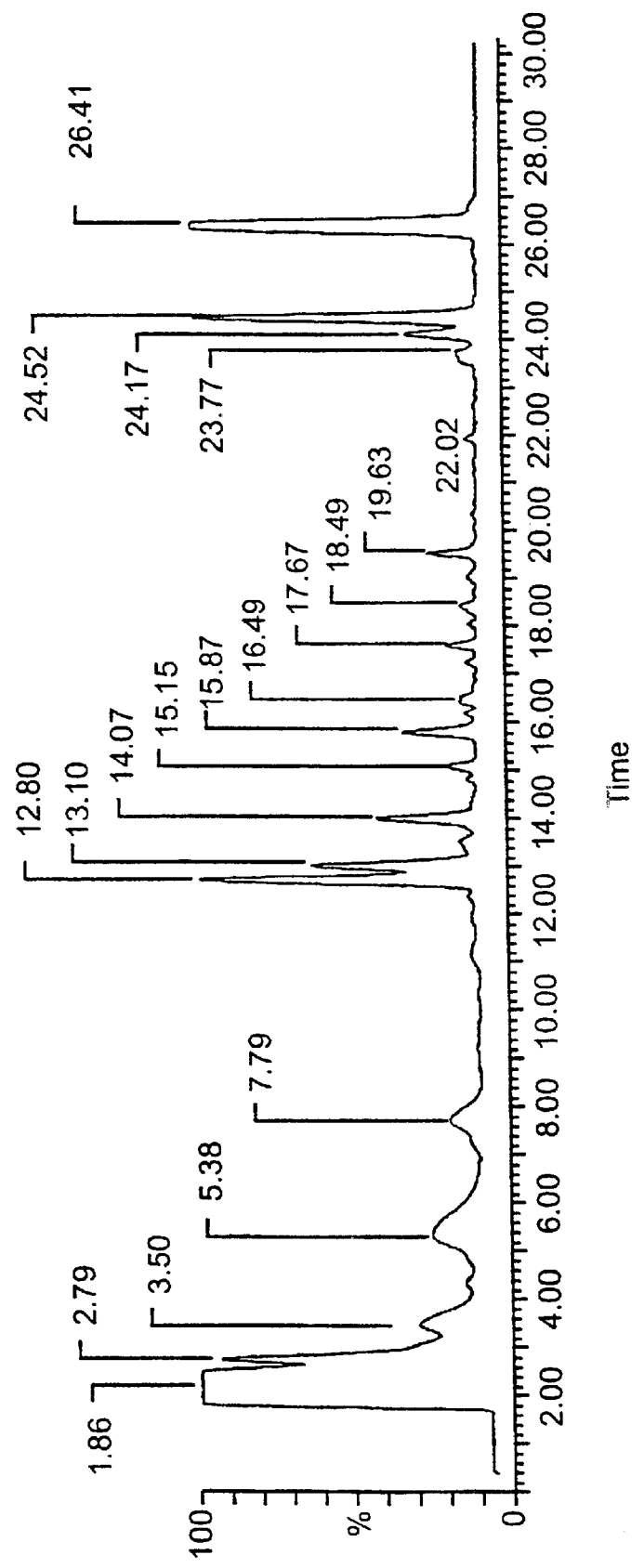
FIGS. 1A–1D show reverse phase HPLC profiles of grapefruit juice extract. The elute was monitored by UV detection at 310 nm, Panel A. Reconstructed ion chromatograms for BG [M+H]$^+$ of m/z 339, Panel B; monohydroxylated BG, [M+H]$^+$ of m/z 355, Panel C; bis-hydroxylated BG, [M+H]$^+$ of m/z 373, Panel D.
Figure 1B:
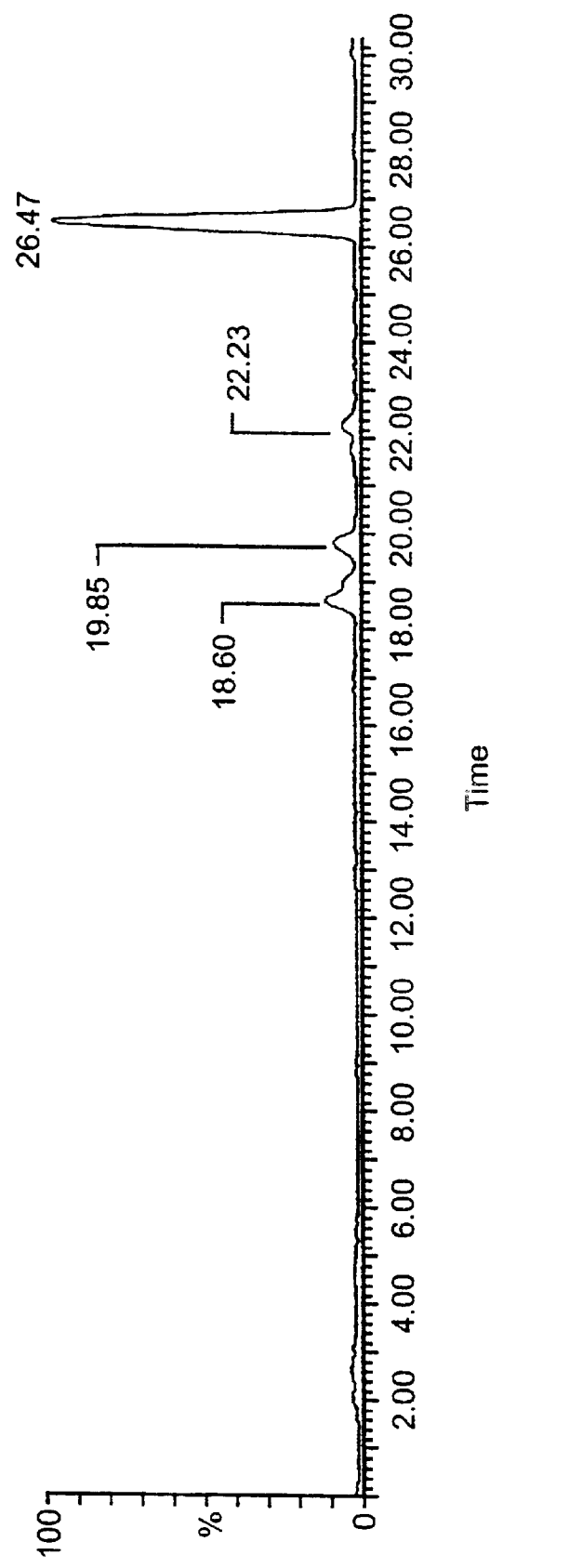
Figure 1C:
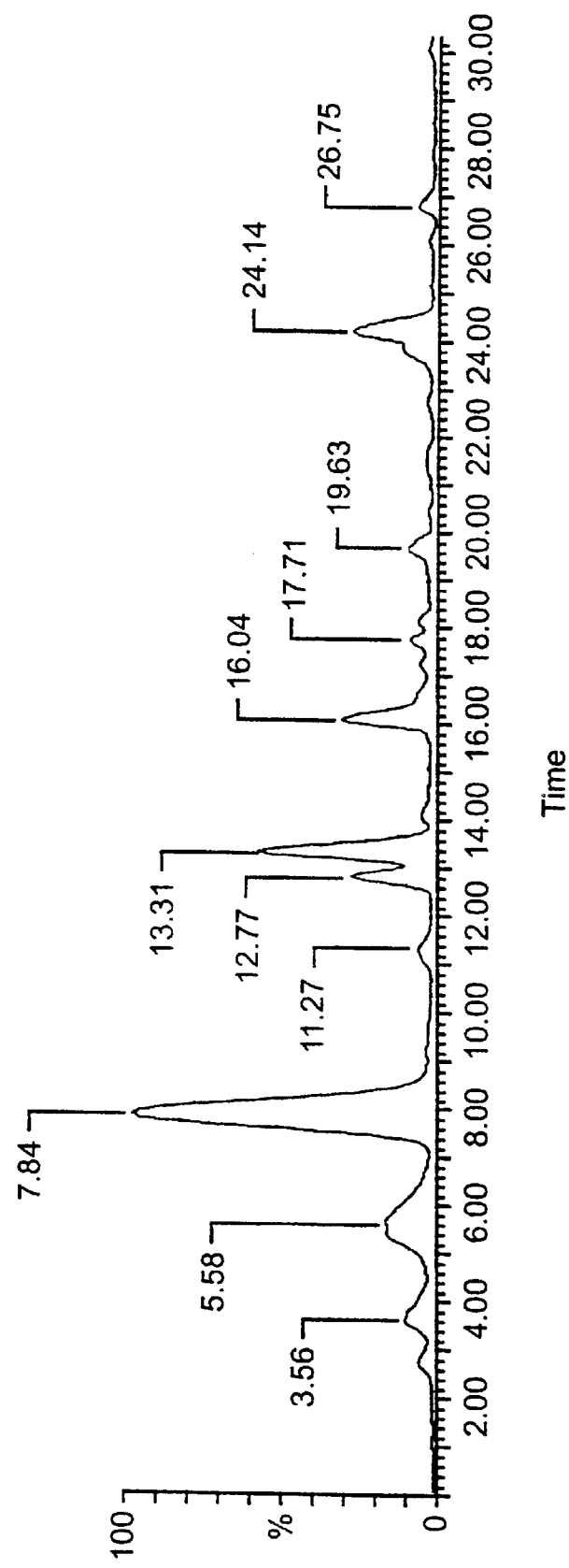
Figure 1D:
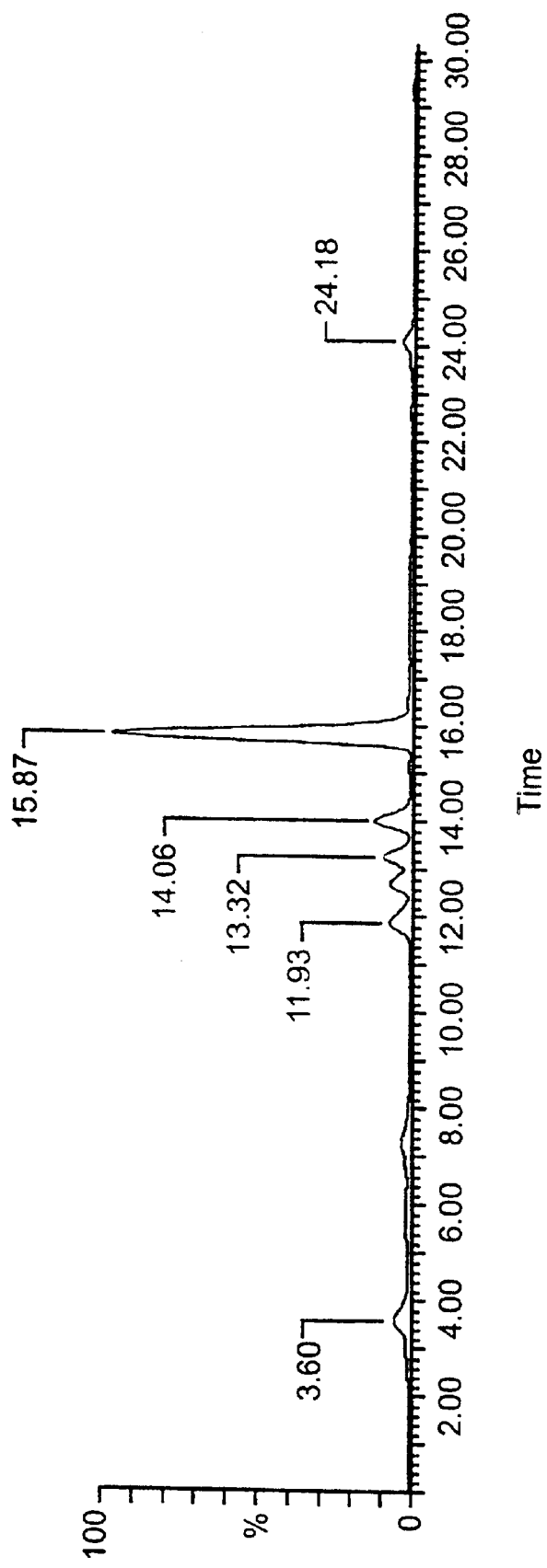

The term "low oral bioavailability" means a compound having oral bioavailability of less than 50%. Preferably less than 30%.

Bergamottin, also known as 5-geranoxypsoralen, bergamotine or bergaptin, is known chemically as (E)-4-[(3,7-dimethyl-2,6-octadienyl)oxy]-7H-furo[3,2-g][1]benzopyran-7-one and has the following chemical structure:

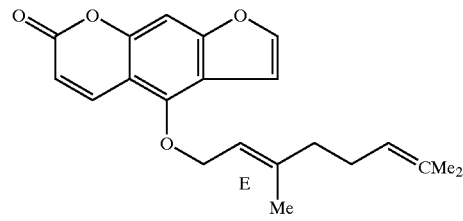

The following Table 1 provides a list of abbreviations and definitions thereof used in the present invention.

TABLE 1

| Abbreviation | Definition |
| --- | --- |
| NADPH | Nicotinamide adenine dinucleotide |
| GSH | Glutathione |
| LC/UV | Liquid chromatography/ultra violet spectroscopy |
| LC/MS | Liquid chromatography/mass spectroscopy |
| HPLC | High performance liquid chromatography |
| ESI | Electrospray ionization |
| CID | Collision-induced dissolution |
| MgCl$_2$ | Magnesium chloride |
| EDTA | Ethylenediaminetetraacetic acid |
| CO | Carbon monoxide |
| BG | Bergamottin |
| IC$_{50}$ | Median inhibition concentration |
| K$_{inactivation}$ | Maximal rate constant of inactivation |

TABLE 1-continued

| Abbreviation | Definition |
| --- | --- |
| $K_I$ | Concentration required for half-maximal inactivation |
| P450 | Cytochrome P450 |

Bergamottin has been identified as a primary compound in grapefruit juice responsible for the mechanism-based inactivation of P450 3A4. Several monooxygenated or dihydroxylated BG derivatives were also identified in grapefruit juice. The content of dihydroxybergamottins, one of them previously isolated and identified for inhibiting testosterone 6β-hydroxylase in rat liver microsomes (Edwards, Supra, 1996), was determined to be less than 20% of the content of BG in grapefruit juice. Most of the BG derivatives in grapefruit juice contain the intact furanocoumarin group which is presumed to be responsible for the inactivation of P450s. Bergamottin and its mono- or dihydroxylated derivatives were not observed in orange juice, which is consistent with reports that orange juice does not cause such inhibitory effects on intestinal drug metabolism (Bailey, Supra., 1991). The content of BG and its derivatives may vary significantly among different preparations of grapefruit juice which could account for the discrepancy reported concerning the grapefruit juice effect (Vanakoski J., Mattila M. J., and Seppala T. Grapefruit juice does not enhance the effects of midazolam and triazolam in man. Eur. J. Clin. Pharmacol., 1996;50:501–508).

The inactivation of P450 3A4 activity was time and concentration dependent as well as requiring metabolism of BG. These results suggest that BG is a mechanism based-inactivator of P450 3A4 (Walsh C. T. Suicide substrates, mechanism-based enzyme inactivation: recent developments. Ann. Rev. Biochem., 1984;53:493–535). Several other furanocoumarins have previously been reported to cause mechanism based-inactivation of P450s, e.g. corandrin (Cai Y., Baer-Dubowska W., Ashwood-Smith M. J., Ceska O., Tachibana S., and DiGiovanni J. Mechanism-based inactivation of hepatic ethoxyresorufin O-dealkylation activity by naturally occurring coumarins. Chem. Res. Toxicol., 1996;9:729–736) and 8-methoxypsoralen (Labbe G., Descatiore V., Beaune P., Letteron P., Larrey D., and Pessayre D. Suicide inactivation of cytochrome P-450 by methoxsalen. evidence for the covalent binding of a reactive intermediate to the protein moiety. J. Pharmacol. Exp. Ther., 1989;250:1034–1042 and Mays D. C., Hilliard J. B., Wong D. D., Chambers M. A., Park S. S., Gelboin H. V., and Gerber N. Bioactivation of 8-methoxypsoralen and irreversible inactivation of cytochrome P-450 in mouse liver microsomes: modification by monoclonal antibodies, inhibition of drug metabolism and distribution of covalent adducts. J. Pharmacol. Exp. Ther., 1990;254:720–731). The furan ring was suggested to be the group responsible for the inactivation of P450 1A based on the studies of a series of naturally occurred coumarins (Cai, Supra., 1996). Some other furan-containing compounds have also been shown to cause inactivation of P450. One example is the furanopyridine L-754,394, a HIV protease inhibitor shown to cause mechanism based-inactivation of P450 3A4 by forming a chemically reactive epoxide on the furan ring (Chiba M., Nishine J. A., and Lin J. H. Potent and selective inactivation of human liver microsomal cytochrome P-450 isoforms by L-754,394, an investigational HIV protease inhibitor. J. Pharmacol. Exp. Ther., 1995;275:1527–1534; Sahali-Sahly Y., Balani S. K., Lin J. H., and Baillie T. A. In vitro studies on the metabolic activation of the furanopyridine L-754,394, a highly potent and selective mechanism-based inhibitor of cytochrome P450 3A4. Chem. Res. Toxicol., 1996;9:1007–1012). BG-mediated mechanism based-inactivation of P450 3A4 is presumed to follow a similar mechanism in which the furan ring is activated to a reactive intermediate which covalently modifies a critical moiety in the active site of the enzyme. The inactivation appears to occur at the active site because it was not inhibited by the addition of 2 or 3 †mM GSH to the incubation system. The value of $K_{inactivation}$ for the BG-mediated inactivation of P450 3A4 of 0.3 min$^{-1}$ indicates that BG is one of the more potent inactivators of P450 3A4. The values of $K_{inactivation}$ for two other potent inactivators are 0.4 min$^{-1}$ for gestodene (Guengerich F. P. Mechanism-based inactivation of human liver microsomal cytochrome P-450 IIIA4 by gestodene. Chem. Res. Toxicol., 1990;3:363–371) and 1.62 min$^{-1}$ for L-754,394 (Chiba M., Supra., 1995;275:1527–1534). In addition, BG was found to be more potent than 6',7'-dihydroxybergamottin whose $K_{inactivation}$ was determined to be 0.16 min$^{-1}$ for the inactivation of P450 3A4 in the reconstituted system. BG also appears to be a competitive inhibitor of P450 3A4. This is consistent with the observation that BG is primarily metabolized to several hydroxylated metabolites by P450 3A4. However, the competitive inhibition may be overestimated because P450 3A4 may have undergone some mechanism based-inactivation by BG during the determination of the testosterone 6β-hydroxylation activity.

Since P450 3A4 activity has been reported to be stimulated by α-naphathoflavone (Ueng Y. F., Kuwabara T., Chun Y. J., and Guengerich F. P. Cooperativity in oxidations catalyzed by cytochrome P450 3A4. Biochemistry, 1997;36:370–381), we investigated the possibility that α-naphathoflavone may have a synergistic effect on the generation of the reactive metabolite of BG which may then lead to increase inactivation. Our results indicate that α-naphatthoflavone had no effect on BG-mediated inactivation of P450 3A4. However, it is not clear whether α-naphathoflavone stimulates the cytochrome P450 3A4 catalyzed hydroxylation of BG.

The mechanism of BG-mediated inactivation of P450 3A4 was preliminarily explored in the present study. Heeme adduct formation is well documented to be the mechanism for inactivation of P450 by terminal olefins and acetylenes (Ortiz de Montellano P. R. and Correia M. A. Inhibition of cytochrome P450. In Cytochrome P450—Structure, Mechanism and Biochemistry (Ortiz de Montellano P. R., Ed. pp 305–366, Plenum Press, New York). Recently, heme adduct formed in a reconstituted system was identified and characterized by visible-spectroscopy, HPLC and mass spectrometry (He K., Falick A. M., Chen B., Nilsson F., and Correia M. A. Identification of the heme adduct and an active site peptide modified during mechanism-based inactivation of rat liver cytochrome P450 2B1 by secobarbital. Chem. Res. Toxicol., 9:614–622 and He K., He Y. A., Szklarz G. D., Halpert J. R., and Correia M. A. Secobarbital-mediated inactivation of cytochrome P450 2B1 and its active site mutants: partitioning between heme and protein alkylation and epoxidation. J. Bol. Chem., 1996;271:25864–25872). The visible spectrum of the BG inactivated P450 3A4 sample showed no sign of heme adduct formation. The only absorption peak observed in the difference spectrum versus the −NADPH control in the range of 400 to 500 nm was at approximately 423 to 425 nm, which is presumed to be due to NADPH-reduced P450. The absorption spectrum also showed that the heme content did not decrease significantly for the BG inactivated P450 3A4 even though the sample lost 90% of the testosterone 6β-hydroxylation activity. This result appears to exclude the other alternative mechanism implicated with several mechanism based-inactivators in which they cause heme fragmentation that leads to covalent binding of the heme fragment to the apoprotein (Ortiz de Montellano, Supra., 1995 and Yao K., Falick A. M., Patel N., and Correia M. A. Cumene hydroperoxide-inactivation of cytochrome P450 2B1: identification of an active site heme-modified peptide. *J. Biol. Chem.,* 1993;268:59–65). However, the reduced-CO difference spectrum of P450 3A4 was decreased by approximately 40% following treatment with BG in a reconstituted system. Because there is no evidence for heme destruction or heme adduct formation, it is possible that the bound BG maybe positioned close to the heme moiety by covalent binding to an active site amino acid residue, in such a way that it interferes with the interaction of CO with ferrous heme. Studies on the inactivation of P450 by another furanocoumarin, 8-methoxypsoralen, suggested that covalent binding of 8-methoxypsoralen to apoP450 at active site might account for the loss of the reduced-CO spectrum of P450 (Labbe, Supra., 1989 and Mays, Supra., 1990). HPLC analysis of BG-inactivated P450 3A4 provided indirect evidence suggesting that BG might modify apoP450. Partial loss of apoprotein seems to be a common feature for the P450 enzyme inactivated by modification of the protein when the P450 incubation mixture is analyzed by reverse phase HPLC (Roberts E. S., Hopkins N. E., Alworth D. A., and Hollenberg P. F. Mechanism-based inactivation of cytochrome P450 2B 1 by 2-ethynylnaphthalene: Identification of an active-site peptide. *Chem. Res. Toxicol.,* 1993;6:470–479 and He K., Supra, 1996). It might be expected that some hydrophobic active site amino acid residues of the inactivated P450 are exposed so that they tightly bind to the reverse phase medium as a result of conformation changes induced by covalent binding. Covalent modification of apoP450 was also reported previously to be a mechanism for the inactivation of P450 by some other furanocoumarins (Labbe, Supra., 1989; Cai, Supra, 1996; Mays, Supra, 1990). Therefore, BG-mediated inactivation of P450 3A4 appears to be primarily due to modification of the apoprotein, as has been observed with 2-ethynylnaphalene and 9-ethynylphenanthrene for the mechanism based inactivation of P450 2B1 and 2B4 (Roberts E. S., Hopkins N. E., Zaluzec E. J., Gage D. A., Alworth W. L., and Hollenberg P. F. Identification of active-site peptides from 3H-labeled 2-ethynylnaphalene-inactivated P450 2B 1 and 2B4 using amino acid sequencing and mass spectrometry. *Biochemistry,* 1994;33:766–3771 and Roberts E. S., Hopkins N. E., Zaluzec E. J., Gage D. A., Alworth W. L., and Hollenberg P. F. Mechanism-based inactivation of cytochrome P450 2B1 by 9-ethnylphenanthrene. *Arch. Biochem. Biophys.,* 1995;323:295–302).

Although the inhibition or inactivation of P450 3A4 by BG and its derivatives is important for understanding the effect of grapefruit juice on the bioavailability of several clinically used drugs which are known to be extensively metabolized by intestinal P450 3A4, we also determined if BG also inhibits the activities of the other human P450s. BG was shown to inhibit the activities of several human P450s including 1A2, 2A6, 2C9, 2C19, 2D6, and 2E1. Because the grapefruit juice effect appears to be manifested primarily at the level of intestines, the contribution of each P450 enzyme to the effect may be dependent on its expression level in intestines. P450 3A4 is the most abundant intestinal P450 enzyme, whereas the other P450s, such as 1A, 2A, 2C, 2D and 2E, are poorly expressed in intestines (Watkins, Supra., 1987 and Peters W. H. M. and Kremers P. G. Cytochrome P450 in the intestinal mucosa of man. *Biochem. Phamacol.,* 1989;38:1535–1538). We suspect that BG and its derivatives may be poorly absorbed or extensively metabolized in gut so that they have little chance to inactivate or inhibit liver P450s.

Certain clinically used drugs are extensively metabolized by P450 3A4 and thus have a relatively low oral bioavailability (Bertz R. J. and Granneman R, *Clin. Pharmacokinet.,* 1997;32:210–258). Table 2 shows the fraction metabolized and the oral bioavailability of various clinically used drugs. Thus, the poor absorption of these drugs partially results from the first pass metabolism by gut P450 3A4. The oral bioavailability of some of these drugs has been shown to be significantly increased by coadministration with grapefruit juice. We have discovered that oral bioavailability of these drugs can be enhanced by formulation or coadministration with BG, the primary furanocoumarin in grapefruit juice.

Since the expression level of intestinal P450 3A4 varies significantly among individuals, it has been considered to be one of the major factors contributing to inter-individual variability of drug metabolism and drug effects. We have further discovered that such variability may be diminished through inactivation of intestinal P450 3A4 by coadministration of BG.

The following are examples of drugs used clinically which have poor bioavailability: Cyclosporine and Tacrolimus are potent immunosuppressive agents used in transplantation and in the treatment of selected autoimmune disorders. Rapamycin is under clinical development for use in transplantation and in the treatment of autoimmune disorders. All of these agents have been shown to be extensively metabolized by P450 3A4. Cyclosporine, Tacrolimus, and Rapamycin are absorbed poorly with oral bioavailability ranging from 15% to 30%, 15% to 20%, and 10% to 20%, respectively. Saquinavir, an HIV protease inhibitor, is very poorly absorbed with oral bioavailability of 1% to 9%. P450 3A4 has been shown to be the primary enzyme responsible for metabolism of Saquinavir. Other HIV protease inhibitors, such as Indinavir and Ritonavir, are also primarily metabolized by P450 3A4 and have relative low oral bioavailability. Several dihydropyridines used as calcium channel blockers, such as Felodipine, Isradipine, Nifedipine, Nimodipine, and Nisoldipine, are primarily metabolized by P450 3A4. Their poor oral bioavailability (5%–20%) has been shown to be mainly due to first pass metabolism. The oral bioavailability of some of the dihydropyridines has been shown to be increased by coadministration with grapefruit juice. Atorvastatin, a hypolipidemic and hypocholesterolemic agent, is metabolized primarily by P450 3A4. The oral bioavailability is only 14% to 30%. All of these agents may be combined with BG and administered to a patient to increase their oral bioavailability. Additionally, other agents listed in Table 2 may also be combined with BG to increase their oral bioavailability.

TABLE 2

Clinically Used Drugs Which Have Poor Oral Bioavailability That Are Primarily Metabolized by P450 3A4

| Drug | Fraction Metabolized (%) | Oral Bioavailability (%) |
|---|---|---|
| cyclosporine | >90 | 30–15 |
| Tacrolimus (FK506) | >90 | 20–15 |

TABLE 2-continued

Clinically Used Drugs Which Have Poor Oral Bioavailability That Are Primarily Metabolized by P450 3A4

| Drug | Fraction Metabolized (%) | Oral Bioavailability (%) |
|---|---|---|
| Sirolimus(rapamycin) | >90 | 20–10 |
| Indinavir | High | ~30 |
| Ritonavir | >90 | 60–80 |
| Saquinavir | >90 | 1–9 |
| Felodipine | >90 | 15–25 |
| Isradipine | >90 | 15–25 |
| Nicardipine | >90 | 20–30 |
| Nisoldipine | >90 | ~5 |
| Nimodipine | >90 | 15–10 |
| Nitrendipine | >90 | 16–6 |
| Nifedipine | >90 | 40–60 |
| Verapamil | >90 | 20–30 |
| Etoposide | ~50 | 35–70 |
| Tamoxifen | >90 | |
| Vinblastine | >50 | Poor |
| Vincristine | >50 | Poor |
| Taxol | | |
| Atorvastatin | | 14–30 |
| Fluvastatin | ~90 | 50–9 |
| Lovastatin | >90 | <5 |
| Pravastatin | >50 | 25–10 |
| Simvastatin | ~60 | <5 |
| Terfenadine | >90 | ~1 |
| Loratadine | >90 | Low |
| Astemizole | >90 | Low |
| Alfentanil | >90 | Very Low |
| Carbamazepine | >90 | >70 |
| Azithromycin | 30–35 | 35–45 |
| Clarithromycin | >70 | 50–55 |
| Erythromycin | >90 | 30–65 |
| Itraconazole | >90 | 44–55 |
| Rifabutin | >90 | 20–12 |
| Lidocaine | >90 | 25–45 |
| Cisapride | >90 | 35–40 |
| Sertraline | >90 | |
| Pimozide | >90 | <50 |
| Triazolam | >90 | 45–70 |
| Midazolam | >90 | 40–50 |
| Testosterone | >90 | Poor |
| Medroxyprogesterone | >90 | <20 |
| Ergotamine | >90 | <1 |

Figure 2:
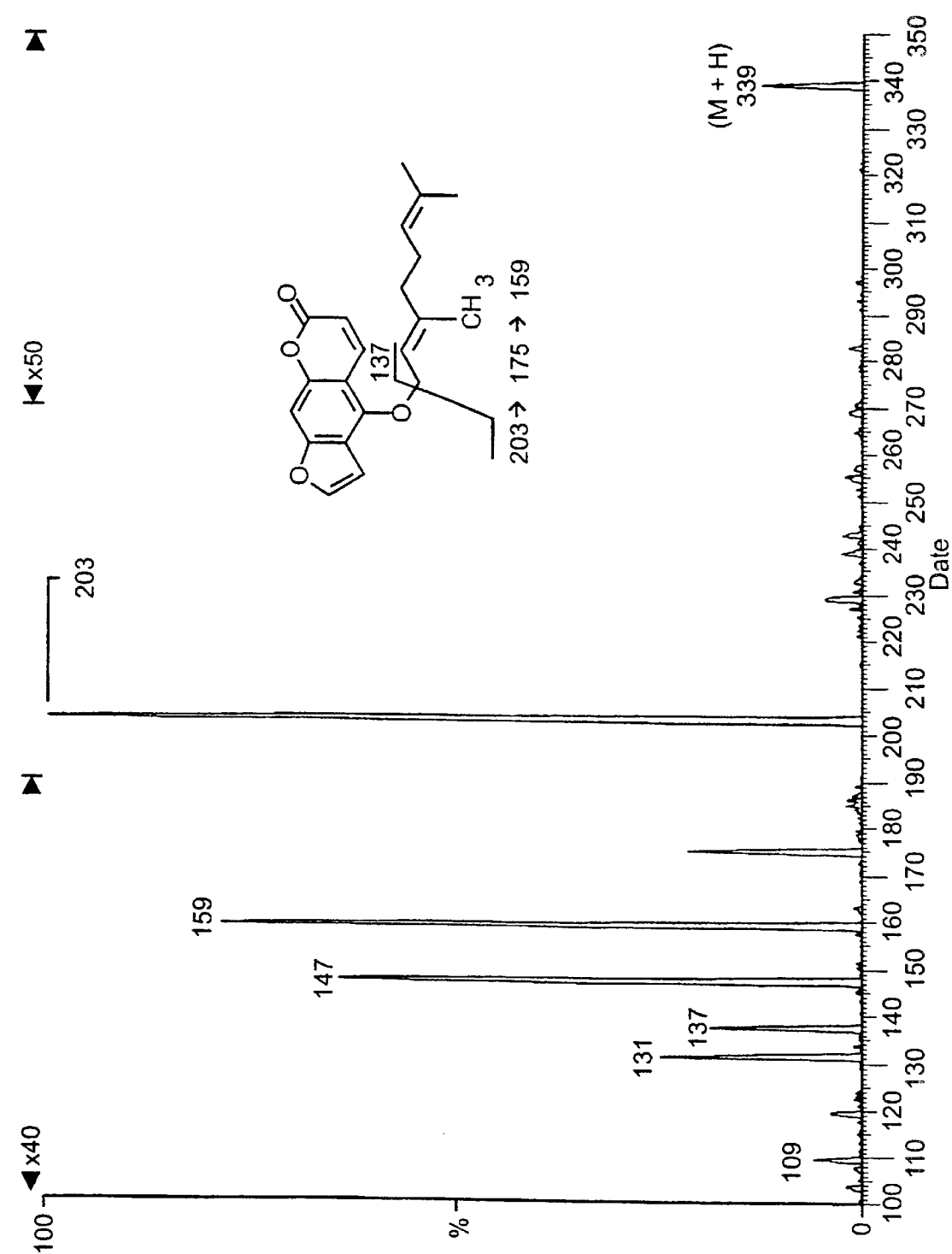
FIG. 2 is a product ion MS/MS spectrum of BG, [M+H]$^+$ of m/z 339.
Figure 3A:
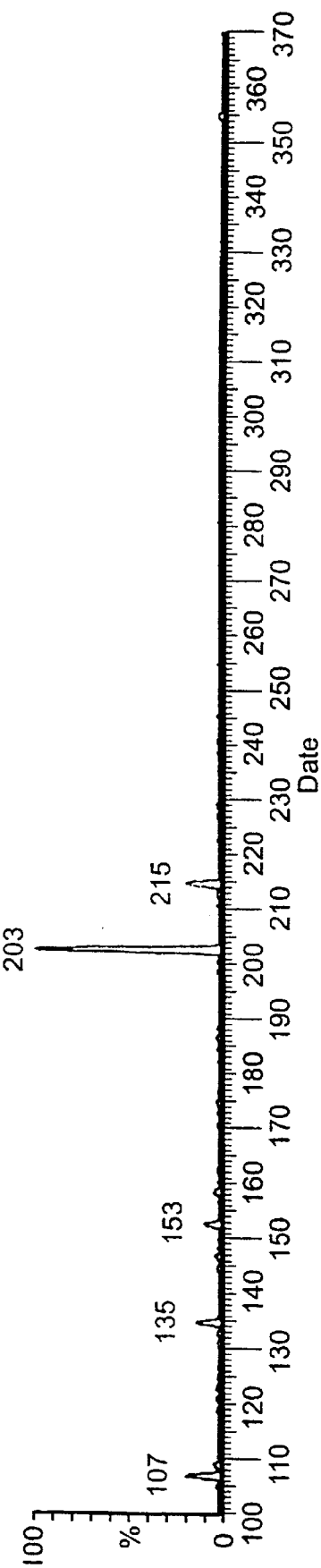
FIGS. 3A–3E are product ion MS/MS spectra of mono-hydroxylated HG metabolites, [M+H]$^+$ of m/z 355. Panel A, 12.9 min (39% relative abundance); Panel B, 17.7 min (6%); Panel C, 18.1 min (11%); Panel D, 19.6 min (7%); Panel E, 24.1 mn (37%). The indicated sites of oxidation are based on the collision induced dissociation behavior of the precursor ion of m/z 355; viz., the product ion of m/z 203 corresponds to the intact 5-hydroxypsoralen moiety and thus, oxidation of the isoprene chain is indicated. Specific sites of oxidation cannot be determined from the MS/MS data.
Figure 3B:
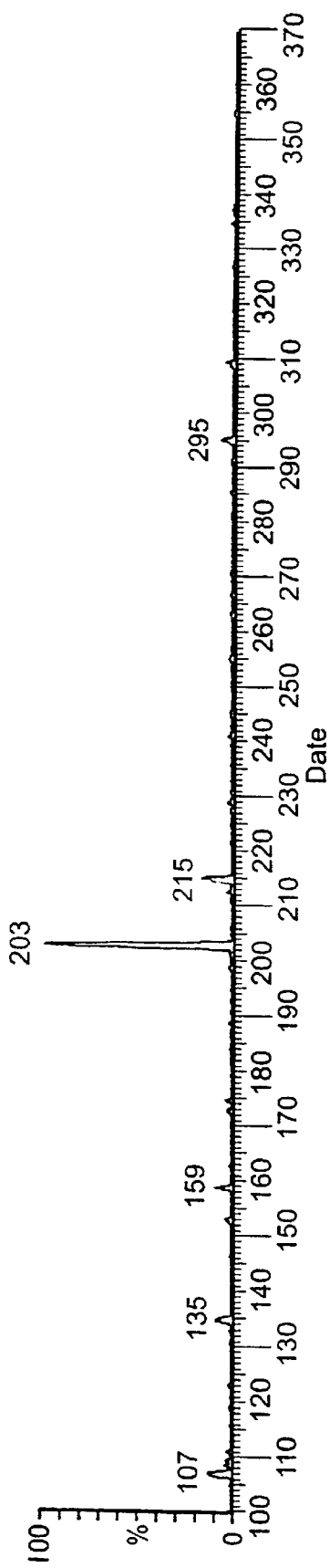
Figure 3C:
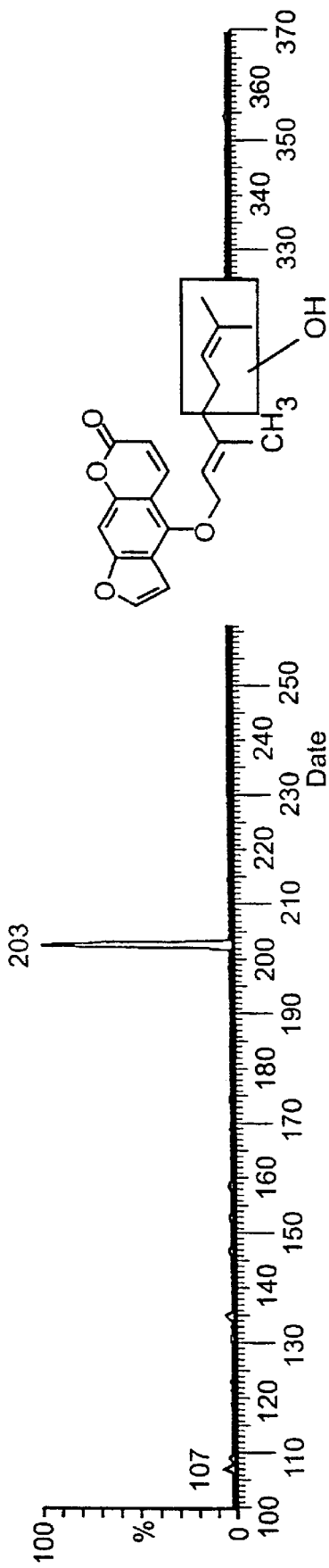
Figure 3D:
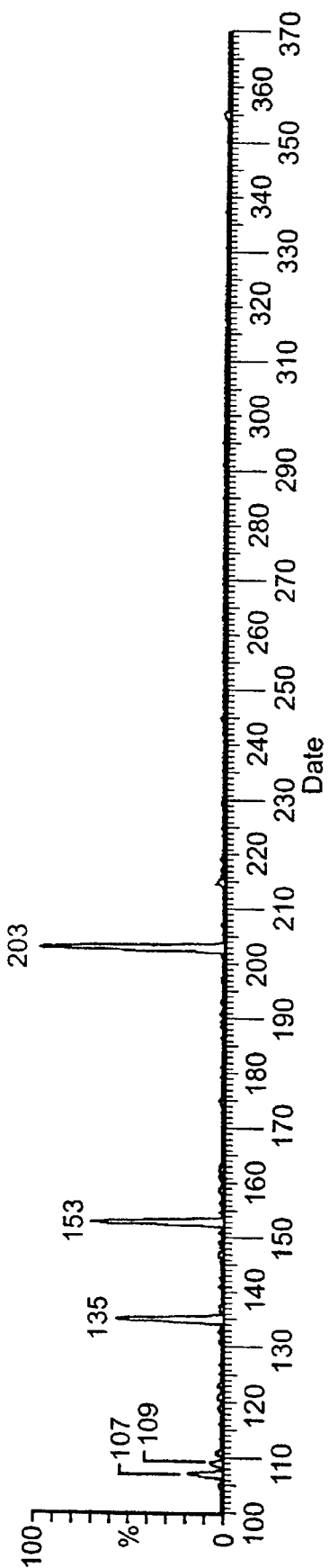
Figure 3E:
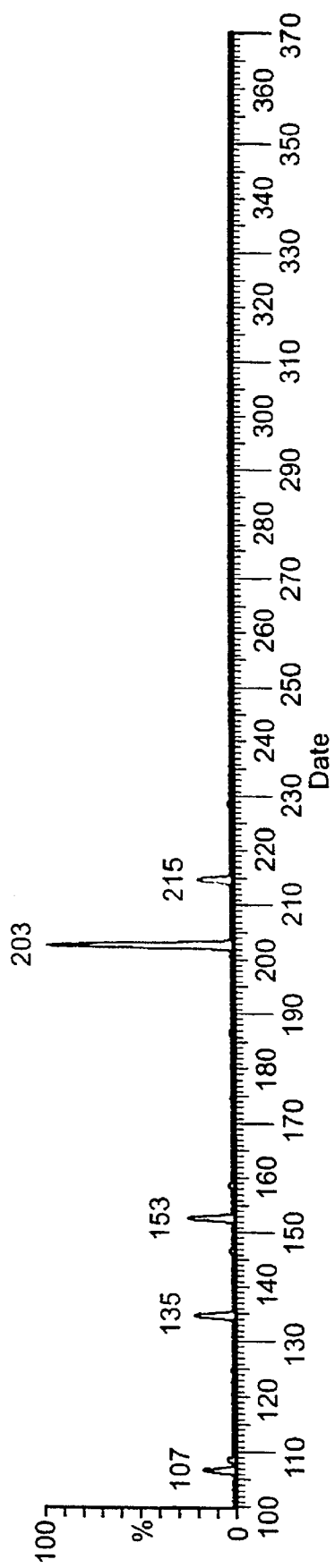
Figure 4A:
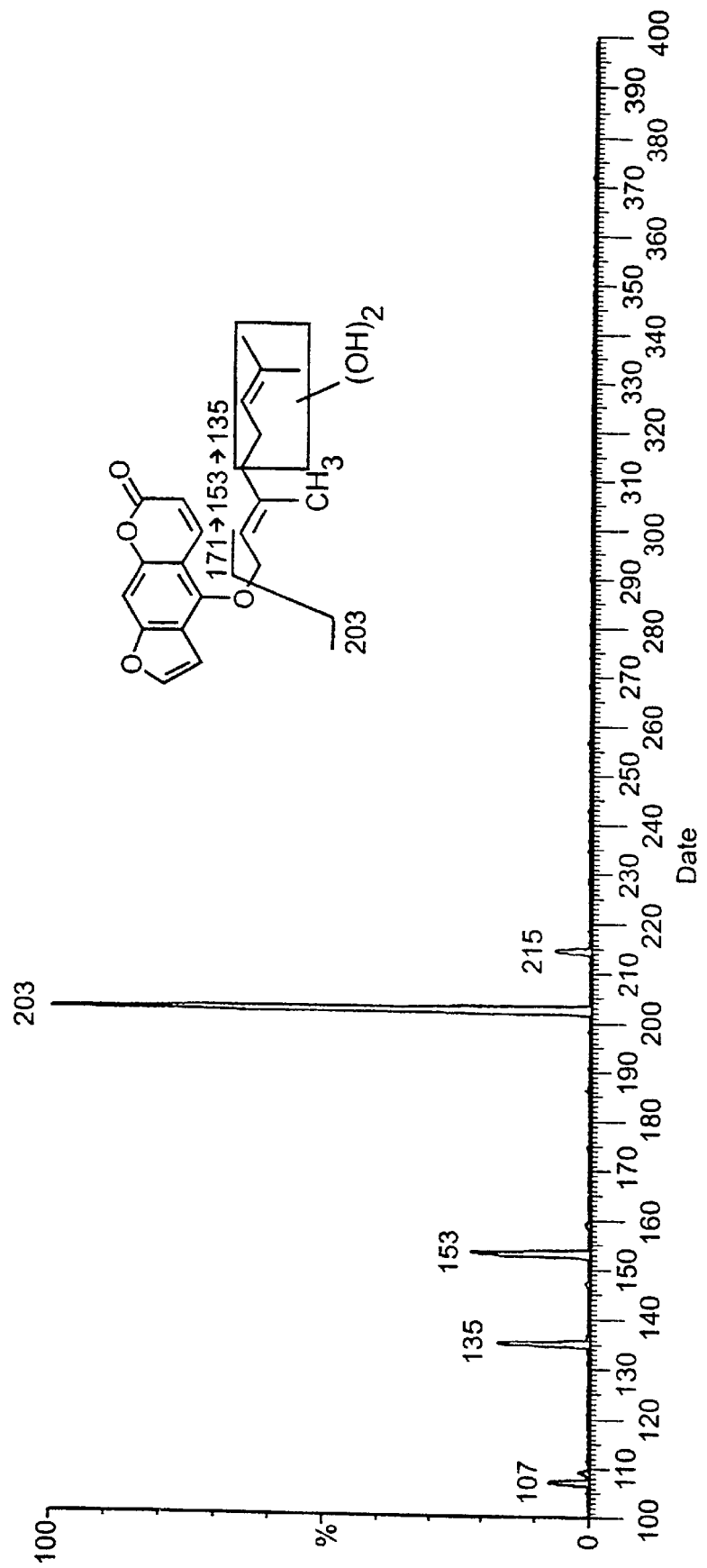
FIGS. 4A–4B are product ion MS/MS spectra of bis-hydroxylated BG, [M+H]$^+$ of m/z 373. Panel A, 12.9 min; Panel B, 15.9 min. %). The indicated sites of oxidation are based on the collision induced dissociation behavior; viz., the ion of m/z 203 (Panel A) corresponds to the intact 5-hydroxypsoralen moiety and thus, oxidation of the isoprene chain is indicated. Loss of formaldehyde (Panel B) to give an ion of m/z 343 was interpreted as indicating aliphatic oxidation. Specific sites of oxidation cannot be determined from the MS/MS data.
Figure 4B:
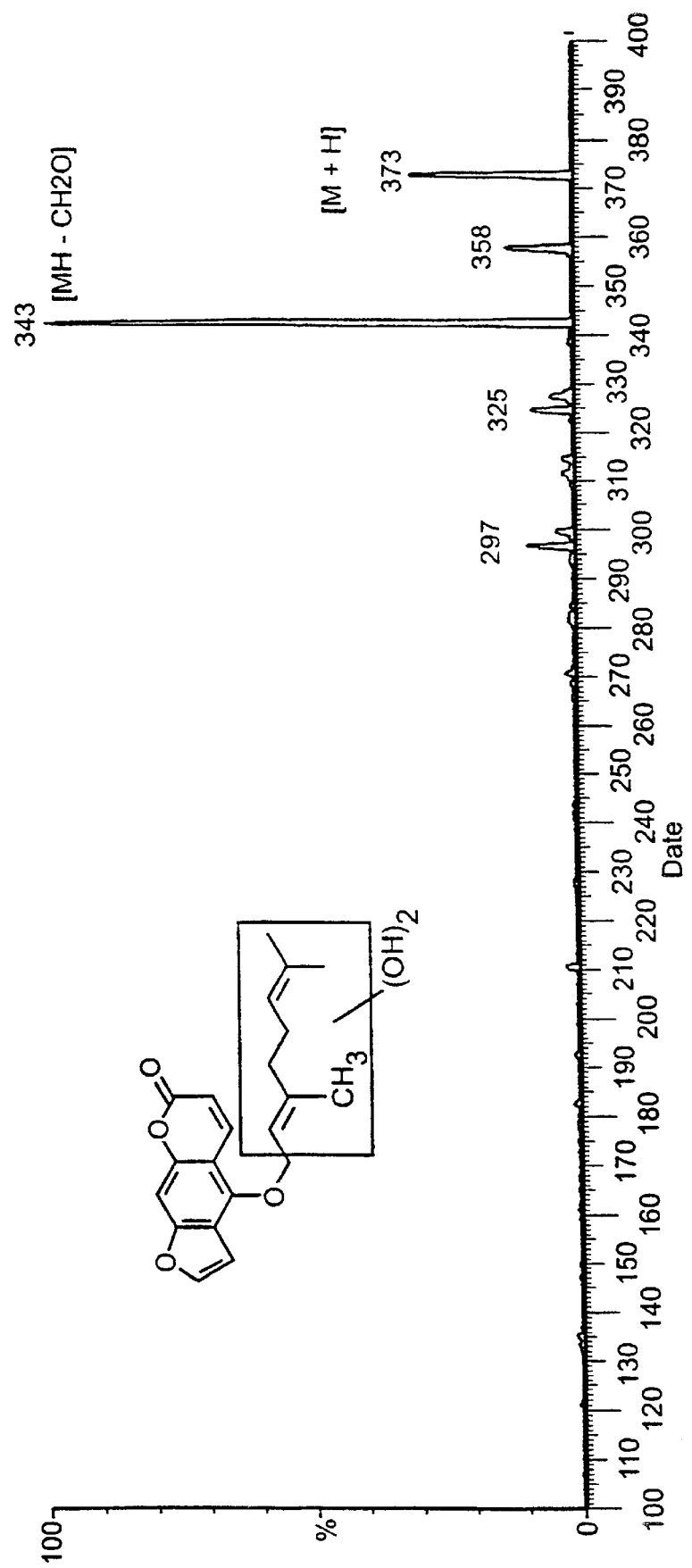

Identification of BG and its derivatives in grapefruit juice: Several components of the ethyl acetate extract of grapefruit juice were separated by HPLC under the conditions described in Methods and Materials (FIGS. 1A–1D). Structural analysis of the component peaks by LC-MS/MS revealed that the peak with a retention time of 26 minutes was BG (FIGS. 1A–1D). The product ion spectrum and HPLC retention time were identical to that of the authentic standard FIG. 2. The predominant fragment ion of m/z 203 corresponds to the 5-hydroxypsoralen moiety which subsequently fragments to give ions of m/z 174, 159, and 147 by loss of CO, $CO_2$, and $C_2H_2O_2$, respectively. The fragment ion of m/z 137 corresponds to the remaining side chain. As shown in FIGS. 1A–1D, there are at least five monooxgenated BG products present in grapefruit juice. Their tentative structures are shown in FIGS. 3A–3E. There are at least two major dihydroxylated BG products in grapefruit juice. The component eluting at 13 minutes had a product ion spectrum and HPLC retention time identical to 6',7'-dihydroxybergarnottin (see FIGS. 4A–4B). The protonated molecular ion of m/z 340 of the component eluting at 24 minutes underwent collision-induced dissociation (CID) fragmentation to give a major product ion of m/z 168 which would suggest that this component is not a derivative of BG. BG itself appears to be the predominant furanocoumarin in the extract of grapefruit juice by ethyl acetate by LC/UV determination. In addition, BG was found to bind to a C18 column so tightly that it was not possible to elute from the column with 60% methanol, the condition previously used to identify 6',7'-dihydroxybergamottin in grapefruit juice (Edwards, Supra., 1996).

LC/UV analysis of the ethyl acetate extracts of orange juice indicated that there is no detectable BG in orange juice.

Figure 5:
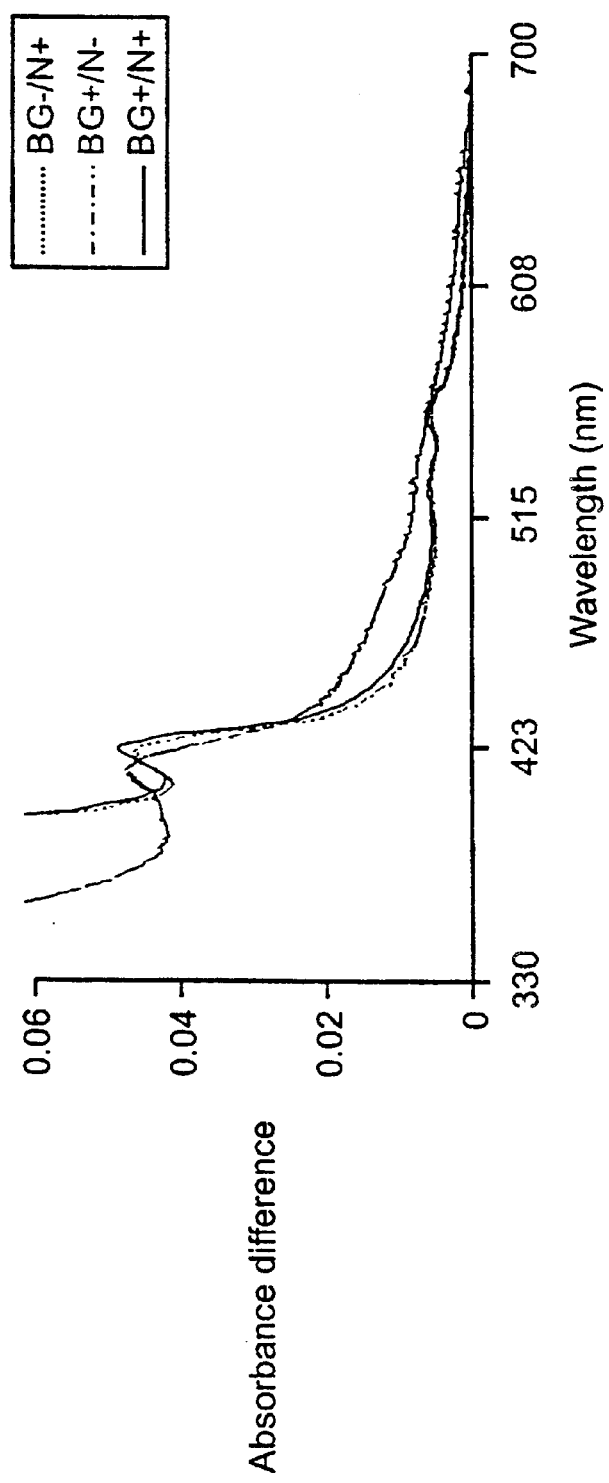
FIG. 5 are reduced-carbon monoxide difference spectra (top panel) and UV-visible spectra (bottom panel) of the reconstituted P450 3A4 reaction mixture incubated with BG in the presence of NADPH (—), with BG in the absence of NADPH (-●-) and without BG in the presence of NADPH (- - -), respectively. P450 3A4 (0.5 nmol/mL) was incubated with 50 µM BG in a reconstituted system at 37° C. for 15 minutes as described in Methods and Materials. Aliquots of 0.25 or 0.2 mL of the incubation mixtures were diluted into 1.75 or 0.8 mL of 50 mM Hepes buffer (pH 7.5) containing 20% glycerol and 0.5 mM EDTA and the reduced-carbon monoxide P450 difference and UV-visible spectra were taken respectively as described in Materials and Methods.

Inactivation of P450 3A4: Incubation of P450 3A4 with BG in the reconstituted system resulted in a 90% loss of the testosterone 6β-hydroxylation activity (Table 3). Approximately 60% of the P450 activity was also inhibited in the absence of NADPH in the reconstituted system (Table 2). However, even when the samples were diluted 20-fold for the determination of testosterone 6β-hydroxylation activity, they still contained 2.5 µM of BG. At this concentration, BG was found to inhibit P450 3A4 activity by approximately 55% in separate experiments. Moreover, P450 contents measured by the reduced-CO spectrum decreased by approximately 40% after 15 minutes incubation of P450 3A4 with BG in presence of NADPH (Table 3). There was no formation of a peak at 420 nm or other absorption instead of that at 450 nm in the range from 400 to 500 nm for the CO-reduced P450 difference spectrum (FIG. 5). The maximum absorption of the absolute spectrum was at 425 nm for BG-inactivated P450 3A4. It was shifted about 2 nm to longer wavelength in comparison with P450 3A4 in the presence of NADPH without BG. There was no indication of heme destruction; however, there was a slight enhancement of the maximum absorption for BG inactivated P450 3A4 (FIG. 5). The P450 content was also decreased to a similar magnitude when −NADPH/+BG sample was used as the reference. This method is considered to diminish the interference in the determination of P450 by CO-generated endogenously during the incubation (Correia M. A., Decker C., Sugiyama K., Underwood M., Bornheim L., Wrighton S. A., Rettie A. E., and Trager W. F. Degradation of rat hepatic cytochrome P 450 heme by 3,5-dicarbethoxy-2,6-dimethyl-4-ethyl-1,4-dihydropyridine to irreversibly bound protein adducts. *Arch. Biochem. Biophys.*, 1987;258:436–451).

Figure 6A:
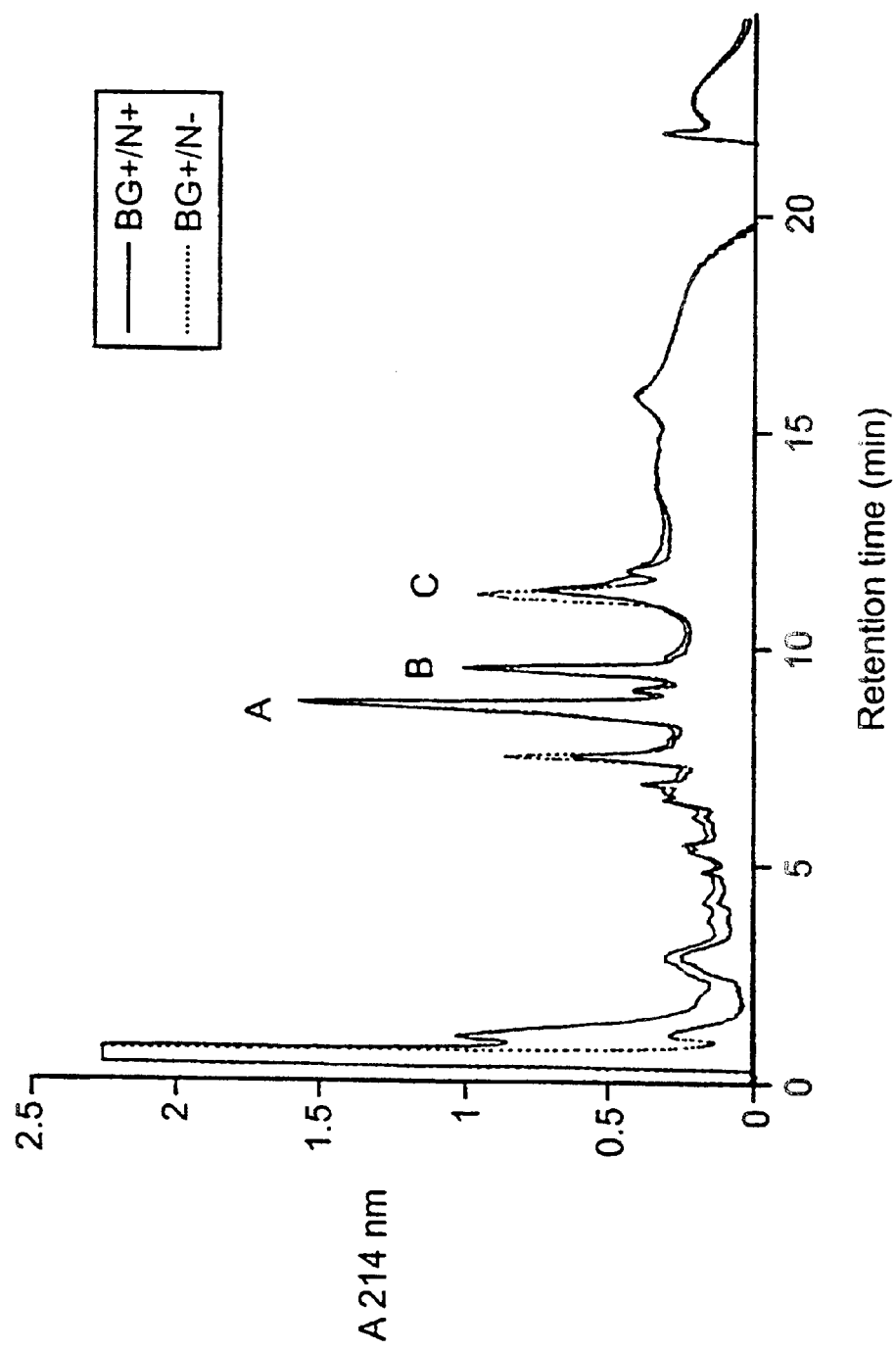
FIGS. 6A–6B are HPLC profiles of the P450 3A4 reconstituted system after incubation with 50 µM BG in the presence (—) or absence of NADPH (—). The eluate was monitored at 214 nm and 405 nm (inset). Peaks A, B, and C represent P450-NADPH reductase, cytochrome b$_5$ and P450 3A4, respectively.
Figure 6B:
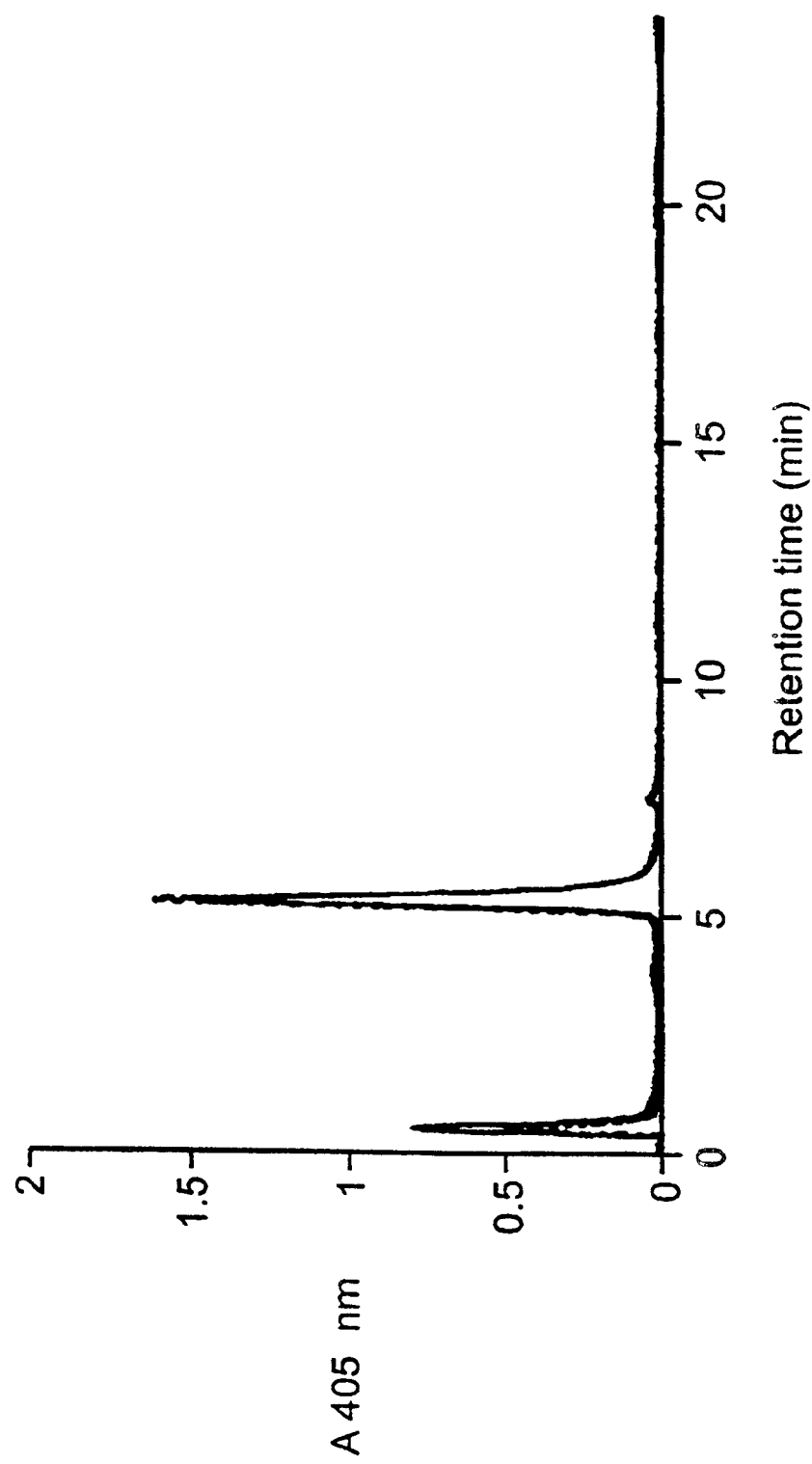

HPLC analysis of BG inactivated P450 3A4: As shown in FIGS. 6A–6B, the amount of apoP450 3A4 was selectively decreased by about 50% when the sample containing P450 3A4 inactivated by BC was analyzed by reverse phase HPLC on a Poros column. Nearly 100% of the reductase and cytochrome $b_5$ protein were recovered from the column when compared with the −NADPH controls. Approximately 90% of the heme was recovered from the sample containing BG inactivated P450 3A4, which was in agreement with the results obtained from the spectral analysis. No modified heme peak could be detected using these BPLC conditions.

Figure 7:
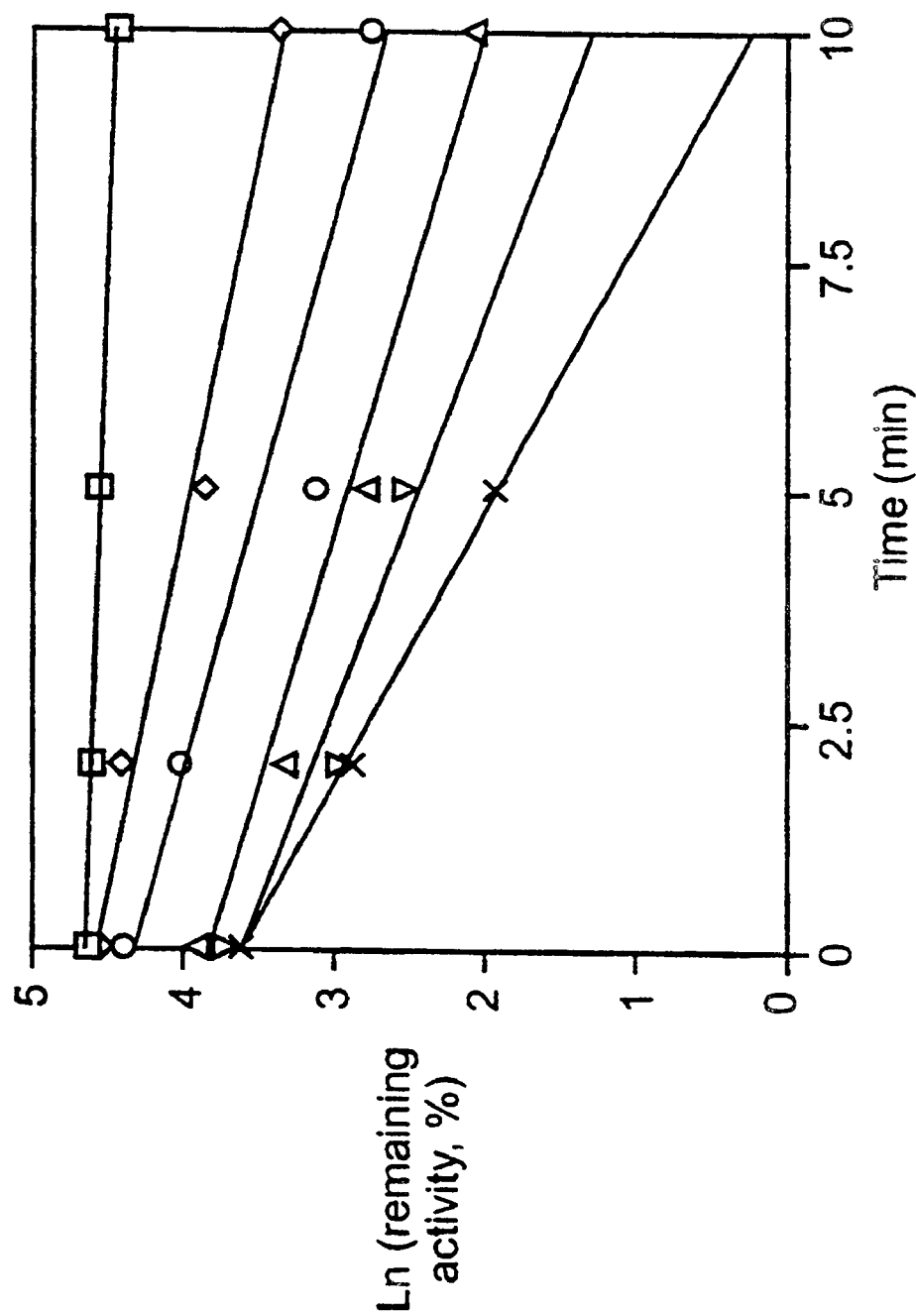
FIG. 7 shows time and concentration dependent inhibition of testosterone 6β-hydroxylation activity of P450 3A4 by BG in a reconstituted system. The experimental details were described in Materials and Methods. The concentration of BG in the preincubation samples were 0 µM (□), 5 µM (◇), 10 µM (○), 25 µM (Δ), 50 µM (∇), and 100 µM (×), respectively.

Time and concentration dependent inactivation of P450 by BG: As shown in FIG. 7, BG mediated inactivation of P450 3A4 in a reconstituted system was time and concentration dependent as well as requiring metabolism of BG. The inactivation exhibited pseudo-first order kinetics with respect to time. Linear regression analysis of the data in FIG. 7 was used to determine the initial rate constants of inactivation ($K_{obs}$). Double-reciprocal plots of the values of $K_{obs}$ and BG concentrations gave a maximal rate constant ($K_{inactivation}$) for inactivation of 0.3 $min^{-1}$ and a concentration of inactivator required for half-maximal inactivation ($K_I$) of 7.7 µM (Walsh, Supra., 1984). A concentration dependent inhibition was also observed for the sample without preincubation. This was consistent with the result from the sample of −NADPH/+BG in Table 3.

Effect of α-naphathoflavone on BG mediated inactivation: α-Naphathoflavone has been reported to stimulate the metabolism of several substrates by P450 3A4 (Ueng, Supra., 1997). Therefore, it was decided to assess whether it would increase the formation of the reactive metabolite of BG, and subsequently enhance inactivation of P450 3A4. α-Naphathoflavone did not change the potency of BG mediated inactivation of P450 3A4. The testosterone 6β-hydroxylation activity of 3A4 was inactivated by about 55% at 2 μM of BG when α-naphathoflavone was simultaneously incubated in the reaction mixture at final concentrations ranging from 6 to 50 μM. Higher concentrations of α-naphathoflavone were not used because of solubility limitation.

Figure 8:
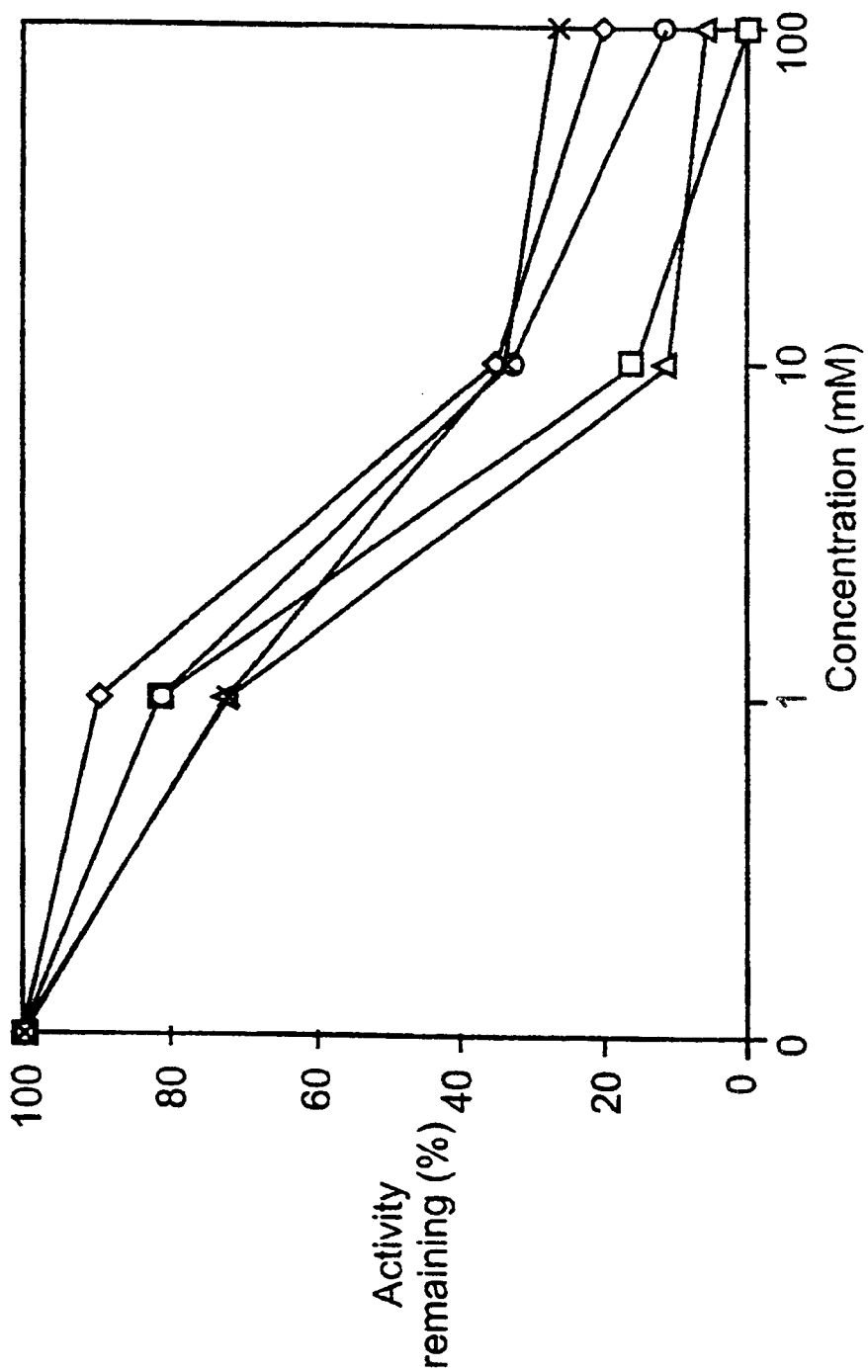
FIG. 8 shows inhibition of BG of the activities of P450s 1A2 ( ), 2A6 (◇), 2C9 (□), 2D6 (Δ), 2E1 (×), and 3A4 (○) in human liver microsomes by BG. The activities of P450 enzymes were determined using the methods described in Materials and Methods. The results were reported as the average of three experiments.

Inhibition of Human Liver Microsomal P450 Enzymes by BG: As shown in FIG. 8, P450s 1A2, 2A6, 2C9, 2D6, 2E1, and 3A4 activities in human liver microsomes were inhibited by BG. The $1C_{50}$s were approximately X, X, 2.4, 3.0, 3.9, and 4.6 μM for P450s 1A2, 2A6, 2C9, 2D6, 2E,1 and 3A4, respectively. Approximately 71% and 100% of P450 2C19 activity were inhibited by 2 and 20 μM of BG, respectively.

TABLE 3

Bergamottin (BG) Mediated Inactivation of P450 3A4 in a Reconstituted System[a]

| | P450 (nmol/mL) | Testosterone 6β-hydroxylation (nmol/min/nmol) |
|---|---|---|
| BG−/NADPH+ | 0.44 | 7.9 |
| BG+/NADPH− | 0.47 | 2.9 |
| BG+/NADPH+ | 0.27 | 0.8 |

[a]P450 3A4 (0.5 nmol/mL) was incubated with 50 μM BG in a reconstituted system at 37° C. for 15 minutes as described in Methods and Materials. An aliquot (0.05 mL) of incubation mixture was diluted into 0.95 mL of 50 mM Hepes buffer (pH 7.5) for the determination of the testosterone 6β-hydroxylation activity.

The compounds of the present invention can be prepared and administered in a wide variety of oral dosage forms.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 100 mg preferably 0.5 mg to 20 mg according to the particular application and the potency of the active component. The composition can, if desired, also contain other compatible therapeutic agents.

In therapeutic use, the compounds utilized in the pharmaceutical method of this invention are administered at the initial dosage of BG of about 0.01 mg to about 1 mg per kilogram daily. A daily dose range of BG of about 0.01 mg to about 0.1 mg per kilogram is preferred. The appropriate therapeutic dosage of the compounds of the present invention which may be combined with BG are known to one skilled in the art. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following nonlimiting examples illustrate the inventors' preferred methods for preparing the compounds of the invention.

MATERIALS AND METHODS

Chemicals: NADPH, L-α-dilauroyl- and L-α-dioleyl-sn-glycero-3-phosphocholines, phosphatidyl serine, catalase, GSH, δ-aminolevulinic acid hydrochloride, testosterone, 6β- and 11β-hydroxytestosterone, chlorzoxazone, coumarin, tolbutamide, were purchased from Sigma Chemical Company (St. Louis, Mo.). 7-Hydroxycoumarin (umbelliferone) was obtained from Aldrich (Milwaukee, Wis.). 4-Hydroxymethyltolbutamide, 6-hydroxychlorzoxazone, 4'-hydroxymephenytoin, racemic bufurolol, and 1'-hydroxybufurolol were obtained from Gentest Corp. (Woburn, Mass.). Isopropyl β-D-thiogalactoside was purchased from Calbiochem Corp. (La Jolla, Calif.). (S)-mephenytoin was a gift from Dr. W. F. Trager (University of Washington, Seattle, Wash.) Bergamottin was purchased from Indofine Chemical Company, Inc. (Somerville, N.J.).

EXAMPLE 1

LC-MS/MS Identification of BG and its Derivatives in Grapefruit Juice

Grapefruit juice or orange juice was made by hand squeezing halved white Florida grapefruits or oranges, respectively. The juice was extracted with ethyl acetate, and the dried extract was dissolved in the HPLC buffer for subsequent analysis. LC/MS identification of the components was performed by using a Quattro II triple quadrupole mass spectrometer (Micromass, Manchester, UK). Sample introduction and ionization was by electrospray ionization (ESI) in the positive ion mode (cone voltage of 30 V). Scan data were acquired under the control of the Micromass Masslynx NT data system (Version 2.22). The components of grapefruit juice were separated by HPLC on a C18 column (Zorbax XDB 5 μm, 2.1×150) eluted with 100 mM acetic acid (A) and acetonitrile (B) by a gradient of 30% B for 5 minutes and then 30% to 70% B within 25 minutes at a flow rate of 200 μL/minute. Molecular weight determinations were performed by acquiring mass spectra over a mass range of 100 to 500 amu at a scan rate of 1.0 second/decade. Determinations of molecular structure were performed by acquiring MS/MS product ion scans at a scan rate of 1.0 second/decade. Collision activation was achieved by using argon at an indicated gas cell pressure of $2.0\times10^{-3}$ torr and collision energy of 20 eV.

EXAMPLE 2

Expression of P450 3A4 and Purification of the Expressed Enzyme

A full-length P450 3A4 cDNA (except for the deletion of codons 3–12 at the 5'-end) engineered into the pCW vector was obtained from Dr. R. W. Estabrook (University of Texas Southwestern Medical Center, Dallas, Tex.). The P450 3A4 containing vector was transformed into MV1304 cells. Growth of the transformed E. coli. was carried out in modified Terrific Broth, and the expression of P450 A4 was induced by addition of 1 mM isopropyl β-D-thiogalactoside. δ-Aminolevulinic acid (0.5 mM) was added to increase heme synthesis. The membrane fraction was prepared from the bacterial cells by sonication after treatment with lysoyme and subsequently isolated from the bacterial cell homogenate by differential centrifugation. P450 3A4 was purified to homogeneity by chromatography on a DE52 column from the detergent solubilized membranes as described previously (Gillam E. M., Baba T., Kim B. R., Ohinori S., and Guengerich F. P. Expression of modified human cytochrome P450 3A4 in *Escherichia coli*. and purification and reconstitution of the enzyme. *Arch. Biochem. Biophys.,* 1993;305:123–131).

EXAMPLE 3

Isolation of NADPH-cytochrome P450 Reductase and Cytochrome $b_5$

NADPH-cytochrome P450 reductase and cytochrome $b_5$ were purified by the methods described previously from liver microsomes of phenobarbital-treated Long-Evans rats (Waxman D. J. and Walsh C. Phenobarbital-induced rat liver cytochrome P450. *J. Biol. Chem.,* 1982;257:10446–10457; Omura T. and Sato R. The carbon-monooxide binding pigment of liver microsomes. *J. Biol. Chem.,* 1964;239:2370–2378).

EXAMPLE 4

BG-mediated Inactivation of P450 3A4 in a Reconstituted System

P450 3A4 (0.5 nmol) was reconstituted with 20 μg of a mixture (1:1:1) of L-α-dilauroyl- and L-α-dioleyl-sn-glycero-3-phosphocholines and phosphatidyl serine, 200 μg of cholic acid, 1 mol of NADPH reductase, 0.5 nmol of cytochrome $b_5$, 500 U of catalase, 2 μmol of GSH, 30 mM $MgCl_2$, 0.5 mM EDTA and 20% glycerol in a final volume of 1 mL of 50 mM Hepes buffer (pH 7.5). Reactions with various concentrations of BG were initiated by addition of 1 mM NADPH, and terminated on ice. The incubations were performed at 37° C. for the time periods indicated. At the end of the incubation, 0.2 mL of the incubation mixture was diluted into 0.8 mL of 50 mM Hepes buffer (pH 7.5) containing 20% glycerol and 0.5 mM EDTA. The spectra were recorded between 330 to 700 nm against the diluting buffer as reference on a DW2-OLIS spectrophotometer in the split beam mode. An aliquot of 0.25 mL was used for the determination of the P450 content by the method of Omura and Sato (Omura and Sato, Supra., 1964). Additional aliquots were taken for determination of testosterone 6β-hydroxylation activity and HPLC analysis.

EXAMPLE 5

Determination of Testosterone 6β-hydroxylation Activity

An aliquot (0.05 mL) of the incubation mixture was diluted into 0.95 mL of 50 mM Hepes buffer (pH 7.5) containing 200 μM of testosterone, 500 U of catalase, 2 μmol of GSH, 30 mM $MgCl_2$, 0.5 mM EDTA and 20% glycerol in a final volume of 1 mL of 50 mM Hepes buffer (pH 7.5), and incubated for 10 minutes at 37° C. 6β-Hydoxytestosterone was determined by HPLC on a C18 column (Microsorb-MV, 5 μm, 4.6×15 cm, Rainin, Woburn) eluted isocratically with a mobile phase of 65% methanol at flow rate of 1 mL/min, and the eluate was monitored by WV detection at 254 nm.

EXAMPLE 6

HPLC Analysis of BG-inactivated P450 3A4

After 10 minute incubation of P450 3A4 with 50 μM of BG in the reconstituted system as described above, 200 μL of the reaction mixture was directly analyzed on a Poros column as described previously (Roberts E. S., Hopkins N. E., Alworth D. A., and Hollenberg P. F. Mechanism-based inactivation of cytochrome P450 2B1 by 2-ethynylnaphthalene: Identification of an active-site peptide. *Chem. Res. Toxicol.,* 1993;6:470–479). The eluate was monitored by UV detection at 14, 310, and 405 nm simultaneously.

EXAMPLE 7

Inhibition of the Activities of Human Liver Microsomal P450 Enzymes by BG

Human liver tissues were obtained from the University of Chicago Distribution Center of LTPADS (Liver Transplant Procurement and Distribution Service, University of Minnesota, Minneapolis, Minn.), Human Biologics Inc. (Phoenix, Ariz.) and the International Institute for the Advancement of Science (Exton, Pa.). The liver microsomes were prepared by differential centrifugation. Caffeine N3-demethylation (Tassaneeyakul W., Mohammed Z., Birkett D. J., McManus M. E., Veronese M. E., Tukey R. H., Quattrochi L. C., Gonzalez F. J., and Miners J. O. Caffeine as a probe for human cytochromes P450: Validation using cDNA-expression, immunoinhibition, and microsomal kinetic and inhibitor techniques. *Pharmacogenetics*, 1992;2:173–183), coumarin 7-hydroxylation (Fentem J. H. and Fry J. R. Metabolism of coumarin by rat, gerbil, and human liver microsomes. *Xenobiotica*, 1992;22:357–367), tolbutamide hydroxylation (Miners J. O., Smith K. J., Robson R. A., McManus M. E., Veronese M. E., and Birkett D. J. Tolbutamide hydroxylation by human liver microsomes: Kinetic characterization and relationship to other cytochrome P-450 dependent xenobiotic oxidations. *Biochem. Pharmacol.*, 1988;37:1137–1144), racemic bufurolol 1'-hydroxylation (Kronbach T., Mathys D., Gut J., Catin T., and Meyer U. A. High-performance liquid chromatographic assays for bufurolol 1'-hydroxylase, debrisoquine 4-hydroxylase, and dextromethorphan o-deethylase in microsomes and purified cytochrome P-450 isozymes of human liver. *Anal. Biochem.*, 1987;162:24–32), chlorzoxazone 6-hydroxylation (Peter R., Bocker R., Beaune P. H., Iwasaki M., Guengerich F. P., and Yang C. S. Hydroxylation of chlorzoxazone as a specific probe for human liver cytochrome P-450 IIEI. *Chem. Res. Toxicol.*, 1990;3:566–573), and testosterone 6β-hydroxylation (Sonderfan A. J., Arlotto M. P., Dutton D. R., McMillen S. K., and Parkinson A. Regulaton of testosterone hydroxylation by rat liver microsomal cytochrome P450. *Arch Biochem Biophys.*, 1987;255:27–41.4) were used to determine the activities of P450s 1A2, 2A6, 2C9, 2D6, 2E1, and 3A4, respectively. Pooled human liver microsomes (N=6, 0.1–1 mg protein/mL) were incubated with BG (1, 10, and 100 μM) in the presence of the corresponding probe substrates, 100 μM caffeine, 4 μM coumarin, 100 μM tolbutarnide, 10 μM bufurolol, 40 μM chlorzoxazone, and 50 μM testosterone in a final volume of 0.5 mL of 0.1 mM phosphate buffer (pH 7.4) at 37° C. for the appropriate time periods, respectively. The reactions were initiated by the additions of 1 mM NADPH and terminated in ice. (S)-mephenytoin 4'-hydroxylation was used for determination of P450 2C19 activity (Meier U. T., Kronbach T., and Meyer U. A. Assay of mephenytoin metabolism in human liver microsomes by high-performance liquid chromatography. *Anal. Biochem.*, 1985;151:286–291). (S)mephenytoin (50 μM) was incubated with pooled human liver microsomes in a final volume of 0.125 mL in presence of 0.2, 2, and 20 μM of BG, respectively. 4'-Hydroxymephenytoin concentration was determined by using LC-MS/MS. Experimental controls consisted of the complete incubation components without the addition of BG.

What is claimed is:

1. A method of inhibiting a human cytochrome P450 enzymatic intestinal metabolism of a Drug having low oral bioavailability in a reconstituted system, comprising administering the drug in combination with isolated form of bergamottin to the reconstituted system.

2. The method according to claim 1 of inhibiting the enzymatic intestinal metabolism involving cytochrome P450 3A4.

3. The method according to claim 1 wherein inhibition of human cytochrome P450 enzymatic intestinal metabolism increases the oral bioavailability of the drug.

4. The method according to claim 1 wherein the oral bioavailability of the drug is less than 50%.

5. The method according to claim 4 wherein the oral bioavailability of the drug is less than 30%.

6. The method according to claim 1 wherein the drug is selected from the group consisting of cyclosporine, Tacrolimus (FK506), Sirolimus(rapamycin), Indinavir, Ritonavir, Saquinavir, Felodipine, Isradipine, Nicardipine, Nisoldipine, Nimodipine, Nitrendipine, Nifedipine, Verapamil, Etoposide, Tamoxifen, Vinblastine, Vincristine, Taxol, Atorvastatin, Fluvastatin, Lovastatin, Pravastatin, Simvastatin, Terfenadine, Loratadine, Astemizole, Alfentanil, Carbamazepine, Azithromycin, Clarithromycin, Erythromycin, Itraconazole, Rifabutin, Lidocaine, Cisapride, Sertraline, Pimozide, Triazolam, Midazolam, Testosterone, Medroxyprogesterone and Ergotamine.

* * * * *